United States Patent
Jang

(10) Patent No.: US 9,572,656 B2
(45) Date of Patent: Feb. 21, 2017

(54) SKIN WEFT AND METHOD FOR MANUFACTURING THE SAME

(71) Applicants: Hoyoung Jang, Incheon-si (KR); Ingoo Park, Incheon-si (KR)

(72) Inventor: Hoyoung Jang, Incheon-si (KR)

(73) Assignees: Hoyoung Jang, Incheon-si (KR); Ingoo Park, Incheon-si (KR)

( * ) Notice: Subject to any disclaimer, the term of this patent is extended or adjusted under 35 U.S.C. 154(b) by 55 days.

(21) Appl. No.: 14/368,290

(22) PCT Filed: Nov. 30, 2012

(86) PCT No.: PCT/KR2012/010344
§ 371 (c)(1),
(2) Date: Jun. 23, 2014

(87) PCT Pub. No.: WO2014/073737
PCT Pub. Date: May 15, 2014

(65) Prior Publication Data
US 2014/0379084 A1    Dec. 25, 2014

(30) Foreign Application Priority Data
Nov. 12, 2012 (KR) ........................ 10-2012-0127605

(51) Int. Cl.
*A41G 5/00* (2006.01)
*A61F 2/10* (2006.01)
(Continued)

(52) U.S. Cl.
CPC .............. *A61F 2/10* (2013.01); *A41G 3/0075* (2013.01); *B29C 65/72* (2013.01); *B29C 66/69* (2013.01);
(Continued)

(58) Field of Classification Search
CPC ........ A41G 5/00; A41G 5/004; A41G 5/0066; A41G 5/0013; A41G 5/002; A41G 5/0026; A41G 5/0073; A41G 5/0053; A41G 5/005; A41G 5/008; A41G 5/0086; A41G 5/0046; A41G 3/0083; A61F 2/10
See application file for complete search history.

(56) References Cited

U.S. PATENT DOCUMENTS 3,665,940 A * 5/1972 Schordalides ........... A41G 3/00
132/53
3,835,867 A * 9/1974 Molinario .............. A41G 3/005
132/201
(Continued)

FOREIGN PATENT DOCUMENTS

KR    10-0272114 B1    3/2001
KR    20-0365087 Y1    10/2004
(Continued)

*Primary Examiner* — Robyn Doan
(74) *Attorney, Agent, or Firm* — Im IP Law; C. Andrew Im

(57) ABSTRACT

A skin weft with artificial hair attached thereto to provide various styling options or ample volumetric feeling. The skin weft comprises a stitched portion formed by stitching on a side edge of artificial hair composed of human hair or resin hair, a resin tape welded to a surface of the stitched portion, and a bonding component attached to a surface of the resin tape. The method for manufacturing the skin weft comprises the steps of forming a stitched portion by stitching one side edge of human hair or resin hair arranged and conveyed in the form of a sheet, and supplying a resin tape onto a surface of the stitched portion to form a bonding portion. Automatic mass production is achieved, thereby improving productivity and significantly reducing manufac-
(Continued)

turing costs. Additional means are unnecessary in the manufacturing process, thereby enabling an unskilled person to perform the task.

5 Claims, 8 Drawing Sheets

(51) Int. Cl.
*A41G 3/00* (2006.01)
*B29C 65/72* (2006.01)
*B29C 65/00* (2006.01)
*B29K 101/12* (2006.01)

(52) U.S. Cl.
CPC ......... *A41G 5/0033* (2013.01); *B29K 2101/12* (2013.01)

(56) References Cited

U.S. PATENT DOCUMENTS

| | | | | |
|---|---|---|---|---|
| 3,910,291 A | * | 10/1975 | Kim | A41G 3/0083 132/201 |
| 5,271,420 A | * | 12/1993 | Park | A41G 3/0075 132/53 |
| 5,413,124 A | * | 5/1995 | Incando | A41G 5/008 132/201 |
| 6,000,406 A | * | 12/1999 | Loren | A41G 5/00 132/200 |
| 6,581,609 B2 | * | 6/2003 | Ott | A41G 3/00 132/201 |
| 6,830,054 B1 | * | 12/2004 | Ross-Kuehn | A41G 5/0093 132/201 |
| 8,578,945 B2 | * | 11/2013 | Sasayama | 132/53 |
| 2005/0115581 A1 | | 6/2005 | Choi | |
| 2006/0065281 A1 | * | 3/2006 | Kim | A41G 5/004 132/201 |
| 2008/0236605 A1 | * | 10/2008 | Russo | A41G 5/0066 132/201 |
| 2011/0094530 A1 | * | 4/2011 | Sedillo-Beadell | A41G 5/008 132/201 |

FOREIGN PATENT DOCUMENTS

| | | |
|---|---|---|
| KR | 10-2011-0007841 A | 1/2011 |
| KR | 10-2011-0089647 A | 8/2011 |
| KR | 10-2012-0113303 A | 10/2012 |

\* cited by examiner

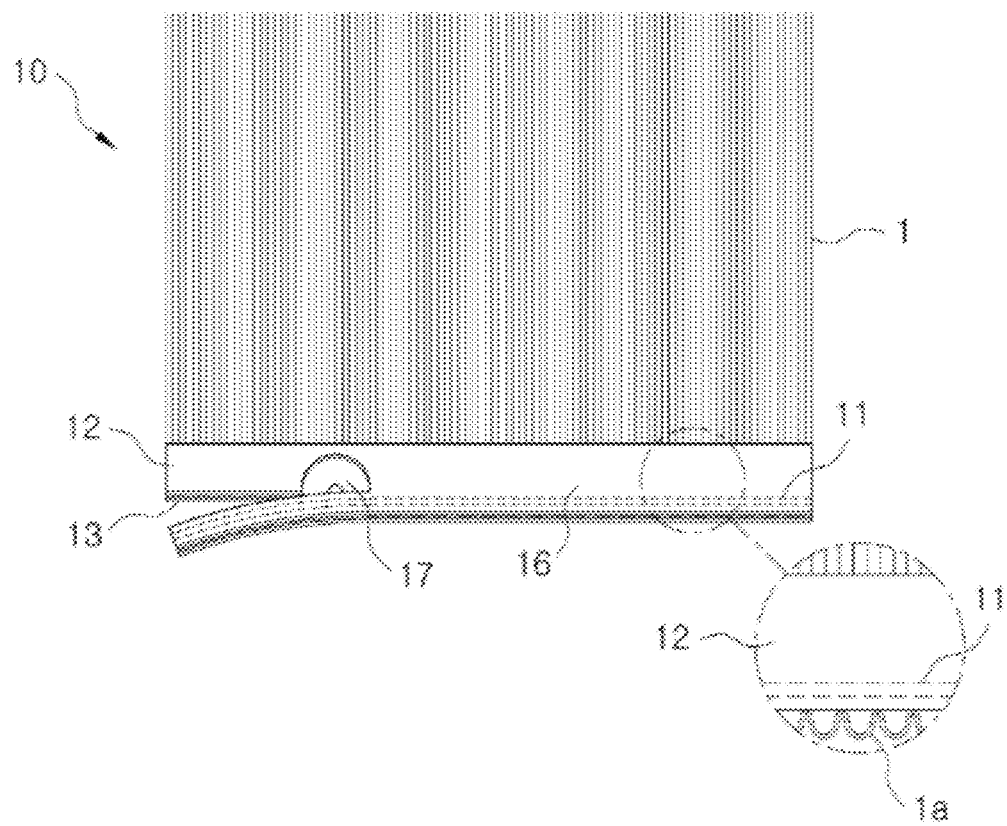
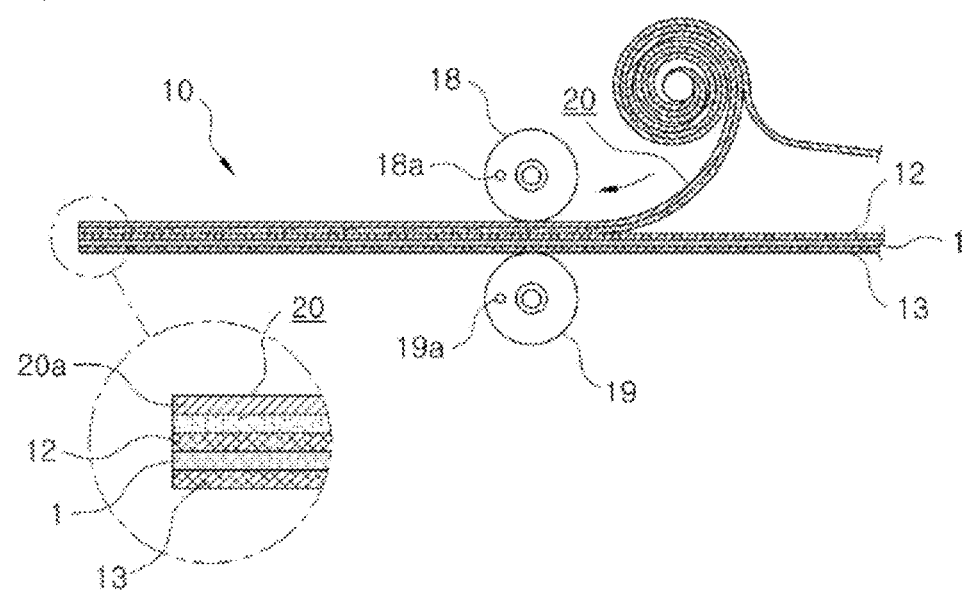

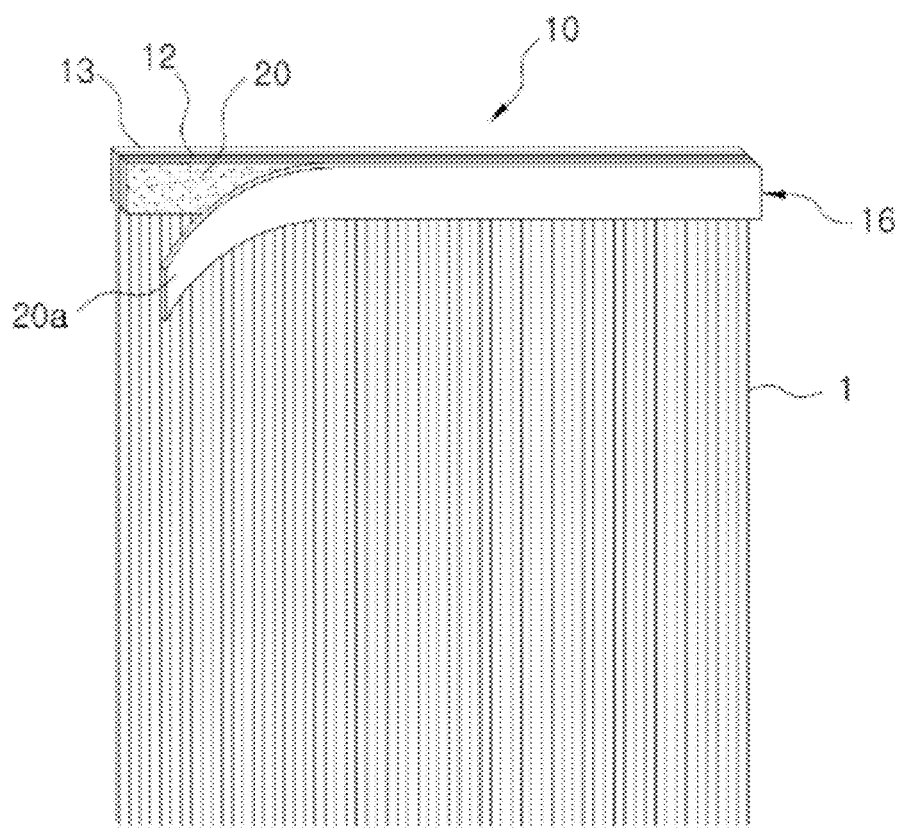

SKIN WEFT AND METHOD FOR MANUFACTURING THE SAME

RELATED APPLICATIONS

This application is a §371 application from PCT/KR2012/010344 filed Nov. 30, 2012, which claims priority from Korean Patent Application No. 10-2012-0127605 filed Nov. 12, 2012, each of which is herein incorporated by reference in its entirety.

BACKGROUND OF THE INVENTION

Field of the Invention

The present invention relates to a skin weft and a method for manufacturing the same, and more particularly, to a skin weft and a method for manufacturing the same that is capable of applying a human or artificial hair extension to a user's hair, thus making it easy to style his or her hair.

Background of the Related Art

If a portion of hair falls out due to hair loss or a quantity of hair is totally small, generally, an artificial or human hair extension is applied to the hair. At this time, if the hair extension made in the form of a small bundle is applied to a user's hair, it is knotted to the user's hair or fixed thereto by means of a separate ring.

However, such knotting needs an operator's skill and long time for the application of the hair extension, and further, if the hair extension is separated from the hair, the hair may be deformed. On the other hand, if the hair extension is fixed to the hair by means of the separate fixing ring, it may be easily separated therefrom due to unstable fixation, or it becomes in an unnatural fixed state.

So as to remove the above-mentioned problems, there has been proposed a skin weft made by attaching artificial hair to a band type bonding portion made of fiber materials having given width and length and applying a loop or adhesive to the bonding portion so as to attach the bonding portion to a user' hair. In case of the conventional skin weft, however, the artificial hair is attached to the bonding portion by means of an adhesive, which is manually manufactured, thus making it hard to achieve mass production. Furthermore, the adhesive should be applied even when the skin weft is applied to a user's hair, thus making it inconvenient to perform the application of the skin weft to the user's hair.

SUMMARY OF THE INVENTION

Accordingly, the present invention has been made in view of the above-mentioned problems occurring in the prior art, and it is an object of the present invention to provide a skin weft and a method for manufacturing the same wherein automatic mass production can be achieved so as to improve productivity and thus significantly reduce manufacturing costs, and it is very convenient to be applied to hair.

To accomplish the above-mentioned object, according to a first aspect of the present invention, there is provided a skin weft including: a stitched portion formed by stitching one side edge of artificial hair made of human hair or resin hair; a resin tape welded to the surface of the stitched portion; and fixing means attached to the surface of the resin tape.

To accomplish the above-mentioned object, according to a second aspect of the present invention, there is provided a method for manufacturing a skin weft including the steps of: forming a stitched portion by stitching one side edge of human hair or resin hair arranged and conveyed in the form of a sheet; and supplying a resin tape onto the surface of the stitched portion and welding the resin tape by heat so as to form a bonding portion.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 6 shows the step of cutting in the method for manufacturing a skin weft according to the present invention;

FIG. 7 shows the step of attaching fixing means in the method for manufacturing a skin weft according to the present invention;

FIG. 8 shows the skin weft produced according to a first embodiment of the present invention;

DETAILED DESCRIPTION OF THE PREFERRED EMBODIMENT

Hereinafter, an explanation on a skin weft and a method for manufacturing the same according to the present invention will be in detail given with reference to the attached drawing.

Figure 1:
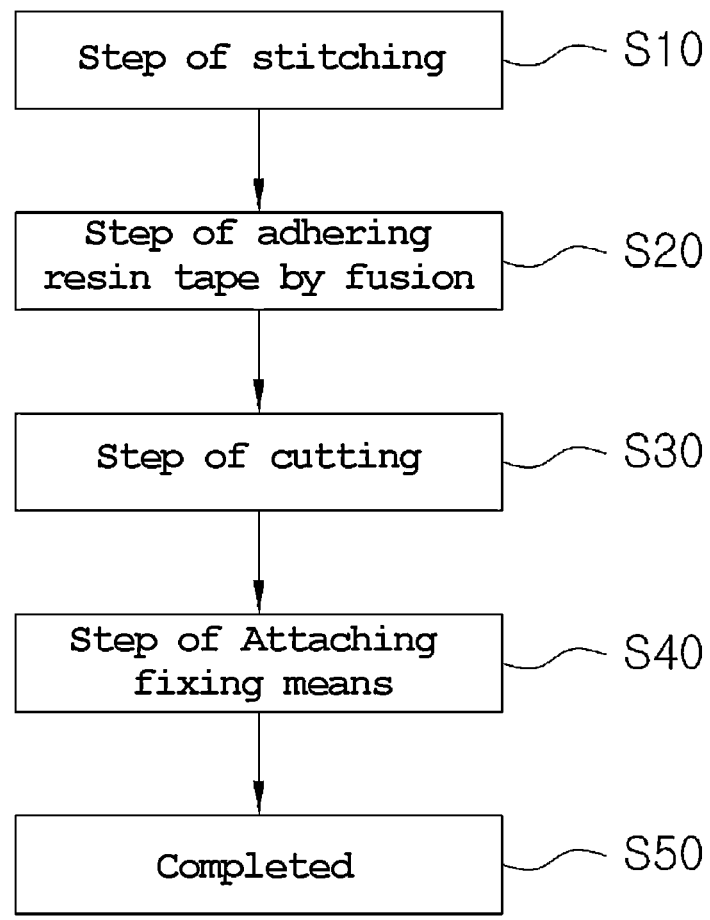
FIG. 1 is a flow chart showing a method for manufacturing a skin weft according to the present invention.

FIG. 1 is a flow chart showing a method for manufacturing a skin weft according to the present invention. First, a stitching process (step S10) is conducted wherein after artificial hair 1 like human hair or resin hair made of synthetic resin is washed and dried, the artificial hair 1 is arranged and conveyed in the form of a sheet so as to form a stitched portion 11 thereon.

Figure 2:
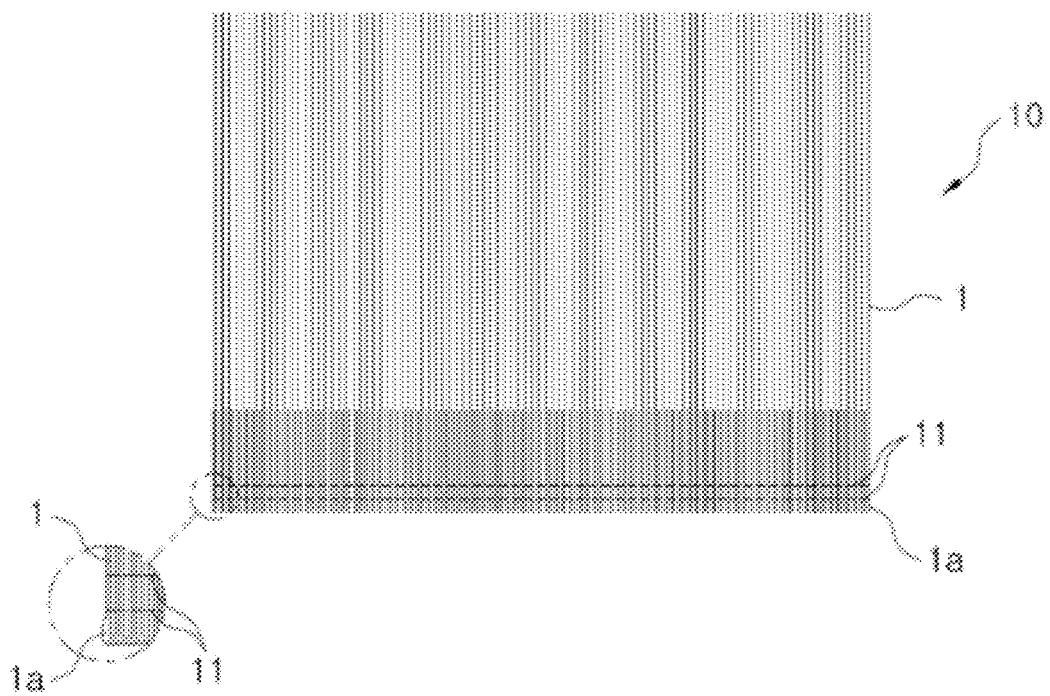
FIG. 2 shows the step of stitching in the method for manufacturing a skin weft according to the present invention.

As shown in FIG. 2, the stitching process (step S10) is conducted to form the stitched portion 11 along the front edge of one side of the artificial hair 1, while the artificial hair 1 is being conveyed, thus making the skin weft 10.

At this time, if the front end of the artificial hair 1, that is, the stitched portion 11 in the stitching process (step S10) is formed by folding the front end portion 1a of the artificial hair 1, a thread is knotted to the front end portion 1a and fixed to a user's hair after the application of the skin weft 10 to the user's hair.

The stitched portion 11 is formed on one side front end edge of the artificial hair 1 by means of one or more stitched lines, and after that, a resin tape welding process (step S20) is conducted wherein while the artificial hair 1 on which the stitched portion 11 is formed is being conveyed, resin tapes 12 and 13 are supplied and welded to both surfaces of the stitched portion 11.

Figure 3:
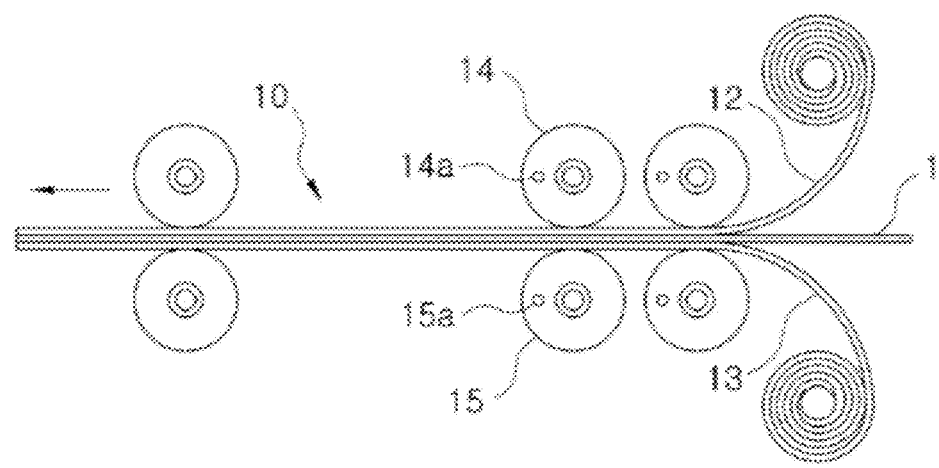
FIG. 3 shows one example of the step of welding a resin tape in the method for manufacturing a skin weft according to the present invention.

As shown in FIG. 3, the resin tape welding process (S20) is conducted by supplying the resin tapes 12 and 13 to top and underside of the stitched portion 11 of the skin weft 10 being conveyed and applying heat to them by means of heating rollers 14 and 15, thus allowing the resin tapes 12 and 13 to be compressed and welded to the top and underside of the stitched portion 11 of the skin weft 10.

The heating rollers 14 and 15 are provided in the form of one set or two sets, and they have heat sensors 14a and 15a mounted at the inside thereof so as to maintain the temperatures of the heating rollers 14 and 15 within a given range.

At this time, the resin tapes 12 and 13 are desirably made of thermoplastic resin dissolved by heat, such as silicone resin, vinyl chloride resin, polyethylene resin, and the like.

When the resin tapes 12 and 13 are passed through the heating rollers 14 and 15, they are heated and compressed at the same time, so that the welding materials produced therefrom are penetrated into the artificial hair 1 and attached thereto.

Figure 4:
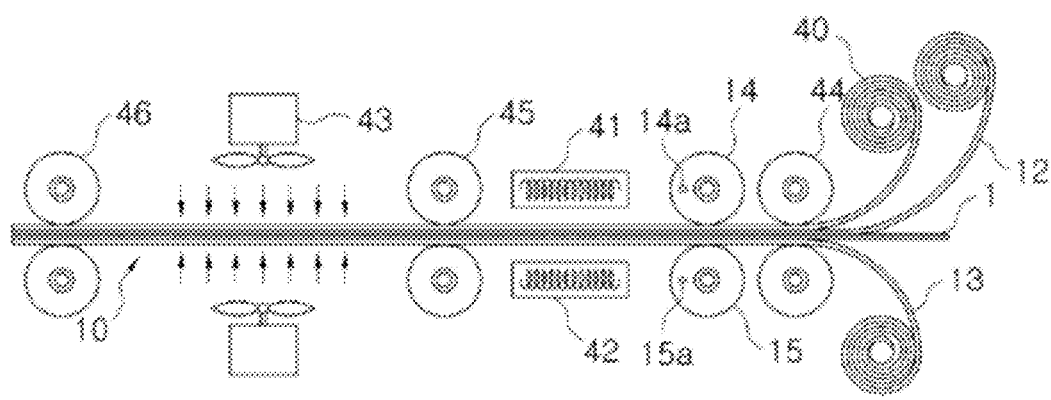
FIG. 4 shows another example of the step of welding a resin tape in the method for manufacturing a skin weft according to the present invention.

The resin tape welding process (step S20) is not limited to the example as shown in FIG. 3, and can be conducted as shown in FIG. 4 wherein while the resin tape 12 and a mesh cloth 40 are being supplied to the top of the stitched portion and the resin tape 13 to the underside thereof, they are first compressed by the heating rollers 14 and 15 and secondarily heated by means of welding means 41 and 42 disposed over and under the artificial hair 1, thus allowing the resin tapes 12 and 13 to be welded to the top and underside of the stitched portion 11 of the skin weft 10.

At this time, if the resin tapes 12 and 13 are dissolved by the welding means 41 and 42, the welding materials produced therefrom are penetrated into the artificial hair 1 around the mesh cloth 40 and the stitched portion 11, thus making the fixed state of the artificial hair 1 more rigid.

The welding means 41 and 42 include an electric heater or an ultrasonic welder.

If the welding for the resin tapes 12 and 13 is conducted by means of the welding means 41 and 42, cooling around the stitched portion 11 is conducted by means of cooling means 43, so that the welded portions of the resin tapes 12 and 13 become solidified and fixed.

A plurality of conveying rollers 44, 45 and 46 is disposed on both side front ends and center in the figure so as to convey and guide the skin weft 10.

Figure 5:
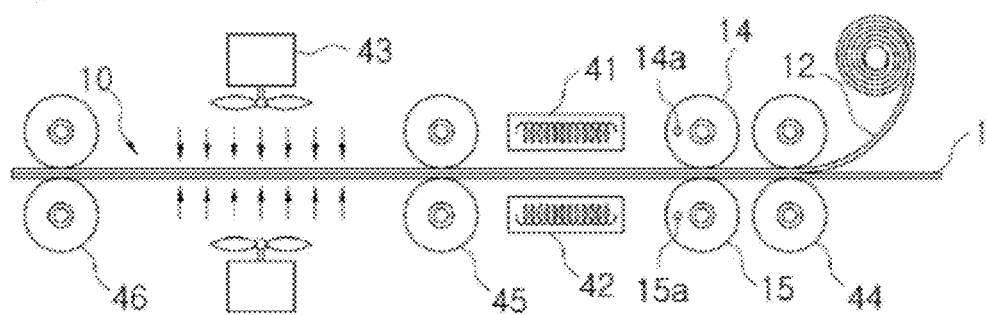
FIG. 5 shows yet another example of the step of welding a resin tape in the method for manufacturing a skin weft according to the present invention.

Further, the resin tape welding process (step S20) can be conducted as shown in FIG. 5 wherein while only the resin tape 12 is being supplied to the top of the stitched portion 11 of the artificial hair 1, it is pre-heated by the heating rollers 14 and 15, welded by means of welding means 41 and 42, and cooled by means of the cooling means 43.

Like this, if the resin tape 12 is welded to one side of the artificial hair 1, the welded surface of the resin tape 12 faces the surface of the hair to which the skin weft 10 is applied, so that it is not seen to the outside, thus removing the lightening on the welded surface of the resin tape 12 formed by the heating roller 14.

The skin weft 10 onto which the resin tapes 12 and 13 are welded through the resin tape welding process (step S20) can be applied in practical use, and as shown in the enlarged portion of FIG. 6, a well-known fixing thread is knotted to the front end portion 1a formed along the front end of the skin weft 10 so as to apply the skin weft 10 to a user's hair.

Next, a cutting process (step S30) is conducted wherein if bonding portions 16 are formed through the welding of the resin tapes 12 and 13 on top and underside of the stitched portion 11, the front ends of the bonding portions 16 are cut constantly.

As shown in FIG. 6, the cutting process (S30) is conducted by cutting the front ends of the bonding portions 16 of the skin weft 10 by a given width by means of a cutter 17.

If the cutting process (S30) is conducted, a fixing means attaching process (step S40) is conducted to attaching fixing means for fixing the skin weft 10 to head or hair to the bonding portions 16 of the skin weft 10.

In the fixing means attaching process (S40), the fixing means for fixing the skin weft 10 to the head surface or hair is attached to one side surface of the bonding portion 16. If the fixing means includes a double-sided tape 20, as shown in FIG. 7, the double-sided tape 20 is attached to the top side of the skin weft 10 and passed between heating rollers 18 and 19 disposed on the top and underside of the skin weft 10, so that the double-sided tape 20 is bonded to the bonding portion 16, while being heated and compressed on the top of the bonding portion 16, thus completing the manufacturing of the skin weft 10.

At this time, the heating rollers 18 and 19 have heat sensors 18a and 19a mounted at the inside thereof so as to prevent them from being heated over a given temperature.

If the double-sided tape 20 as the fixing means is attached, a protection sheet 20a is separated from the double-sided tape 20, and next, the bonding portion of the double-sided tape 20 is attached to a portion where the skin weft 10 is applied. For example, the attachment of the bonding portion of the double-sided tape 20 is conducted in the state where a user's hair behind his or her hair to which the skin weft 10 is applied is lifted up.

Figure 9:
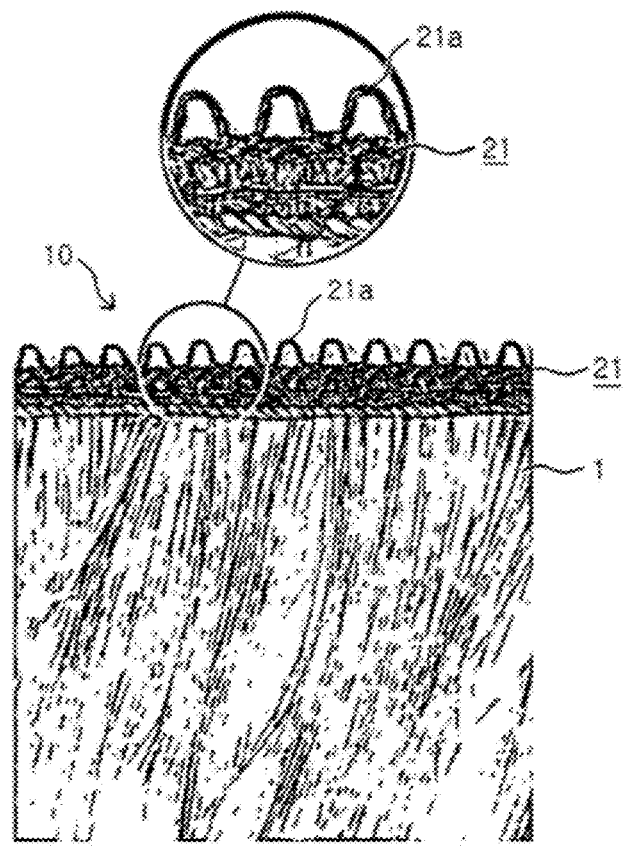
FIG. 9 shows the skin weft produced according to a second embodiment of the present invention.

On the other hand, the fixing means is not limited to the double-sided tape 20, and for example, as shown in FIG. 9, it may be a lace 21 attached to one side surface of the bonding portion 16 by means of sewing or an adhesive, the lace 21 having a plurality of loops 21a formed on the front end of the upper portion thereof. The user's hair is inserted into the loops 21a and fixedly knotted to them. Otherwise, the loops 21a and the user's hair are knotted to each other by means of a separate fixing thread, thus fixing the skin weft 10 to the user's hair.

In this case, the skin weft 10 becomes one piece or has a plurality of pieces connected to each other and is thus applied to the user's hair through the lace 21.

Figure 10:
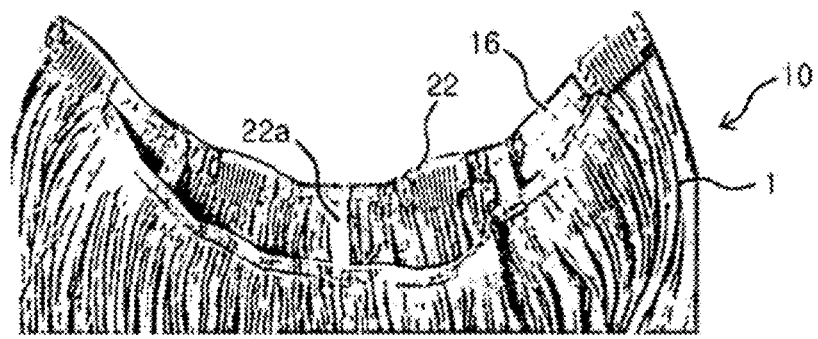
FIG. 10 shows a first application example of the skin weft according to the present invention.

On the other hand, as shown in FIG. 10, the fixing means includes fixing clips 22 coupled to the bonding portion 16, thus applying the skin weft 10 to the user's hair, and in this case, a plurality of skin wefts 10 can be connected with each other by means of connection members 22a like tapes.

Figure 11:
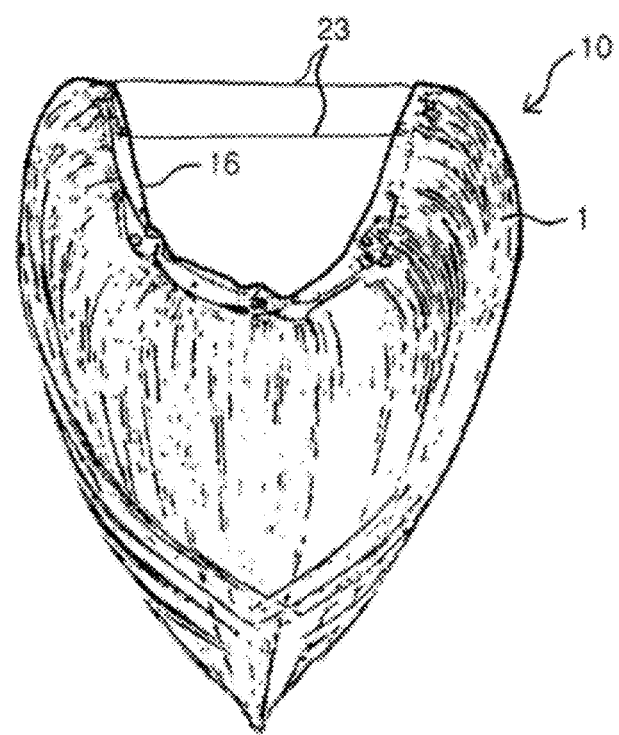
FIG. 11 shows a second application example of the skin weft according to the present invention.

Further, as shown in FIG. 11, the fixing means includes a plurality of fixing strings 24 disposed traversely to each other in such a manner as to allow the skin weft 10 to surround the user's head, thus fixing the skin weft 10 to the user's head.

Figure 12:
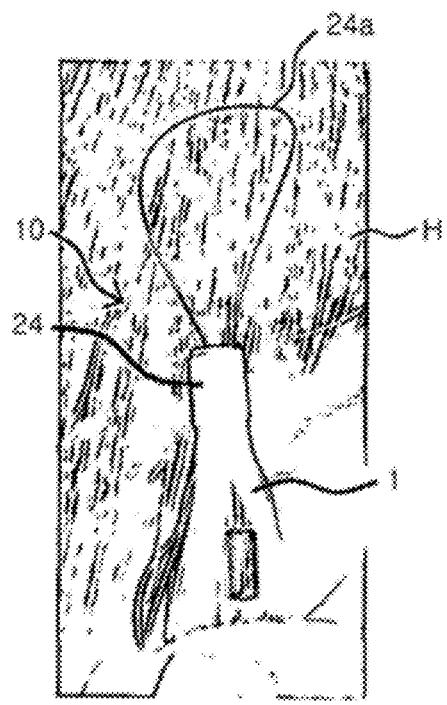
FIGS. 12 and 13 show a third application example of the skin weft according to the present invention.
Figure 13:
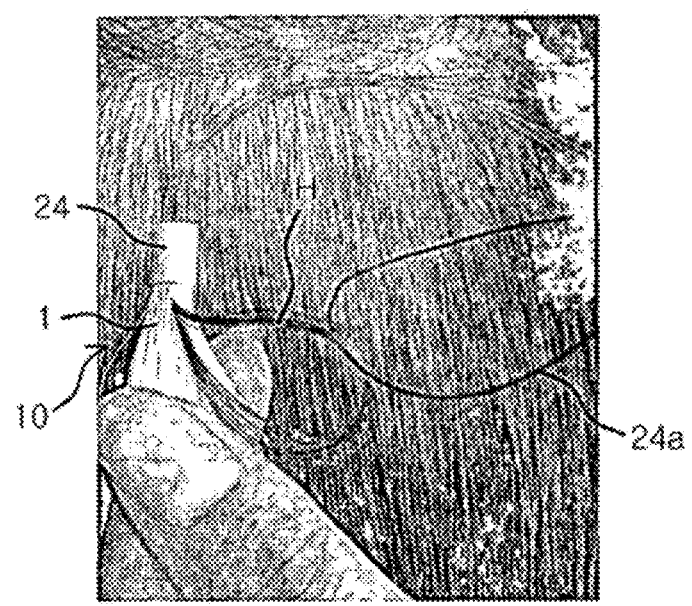

Furthermore, the skin weft 10 is not limited to the application in the spread state thereof, and as shown in FIG. 12, the bonding portion 16 of the skin weft 10 is rolled and fixed to the interior of a fixing ring 24 by means of an adhesive. Next, an application loop 24a is inserted into the fixing ring 24, and as shown in FIG. 13, the user's hair H is inserted into the application loop 24a and pulled and induced to the interior of the fixing ring 24. After that, the skin weft 10 is knotted to the user's hair H or fixed thereto by means of an adhesive.

As mentioned above, the skin weft and the method for manufacturing the same according to the present invention is provided wherein automatic mass production can be achieved so as to improve productivity and thus significantly reduce manufacturing costs, and it is unnecessary to use additional means such as an adhesive, so that the manufacturing process is conveniently and quickly performed, and even an unskilled person can be readily handle it.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method for manufacturing a skin weft comprising the steps of:
    forming a stitched portion by folding a front portion of one side edge of human or resin hair arranged and conveyed in a form of a sheet, and stitching the folded front portion of said one side edge of the human hair or resin hair;
    supplying a resin tape onto a surface of the stitched portion and welding the resin tape by heat so as to form a bonding portion wherein said bonding portion including a total width extending from a top edge to a bottom edge and a total length extending between one side edge to an opposing side edge; said total length being transverse to said total width;
    cutting said bonding portion along a given width of the skin weft, wherein said given width is less than said total width;
    rolling the cut skin weft into a cylindrical shape and attaching it into a fixing ring;
    fixing the cut skin weft to an interior of the fixing ring by an adhesive; and
    inserting an application loop into the fixing ring.

2. The method according to claim 1, further comprising the step of cutting a front end of the bonding portion after the resin tape is welded.

3. The method according to claim 1, wherein the resin tape is made of any one selected from silicone resin, vinyl chloride resin, and polyethylene resin.

4. The method according to claim 1, further comprising the step of welding the resin tape to one side surface or both side surfaces of the stitched portion.

5. The method according to claim 1, further comprising the step of disposing mesh cloth between the stitched portion and the resin tape.

* * * * *